United States Patent [19]

Cahoy

[11] 4,243,407
[45] * Jan. 6, 1981

[54] 2-ACYLAMINOTHIAZOL-4-YLACETAMIDES AS POST EMERGENT SELECTIVE HERBICIDES

[75] Inventor: Roger P. Cahoy, Overland Park, Kans.

[73] Assignee: Gulf Oil Corporation, Pittsburgh, Pa.

[ * ] Notice: The portion of the term of this patent subsequent to Oct. 17, 1995, has been disclaimed.

[21] Appl. No.: 69,026

[22] Filed: Aug. 23, 1979

Related U.S. Application Data

[62] Division of Ser. No. 937,290, Aug. 28, 1978.

[51] Int. Cl.$^3$ ............................................. A01N 43/78
[52] U.S. Cl. ........................................ 71/90; 548/195
[58] Field of Search ............................. 71/90; 548/195

[56] References Cited

U.S. PATENT DOCUMENTS

| | | | |
|---|---|---|---|
| 3,547,917 | 12/1970 | Kulka et al. | 548/194 |
| 3,823,005 | 7/1974 | Doyle et al. | 71/90 |
| 4,120,690 | 10/1978 | Cahoy | 71/90 |
| 4,152,329 | 5/1979 | Cahoy | 71/90 |

*Primary Examiner*—Nicholas S. Rizzo
*Attorney, Agent, or Firm*—Carl A. Cline

[57] ABSTRACT

A class of amides disclosed to be useful as selective pre-emergent and post-emergent herbicides are those having the general structural formula

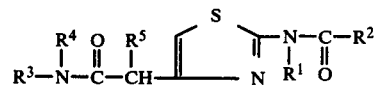

in which $R^1$ is hydrogen or methyl, $R^2$ is ethyl, isopropyl, cyclopropyl, tert.butyl, methylamino, dimethylamino, ethylamino or methoxymethylamino, $R^3$ is phenyl, 4-chlorophenyl, 3,4-dichlorophenyl, 4-methylphenyl or 4-methoxyphenyl, $R^4$ is hydrogen or $C_1$ to $C_3$ lower alkyl, and $R^5$ is hydrogen or methyl, with the further stipulation that either, but not both $R^4$ and $R^5$ may be hydrogen.

7 Claims, No Drawings

2-ACYLAMINOTHIAZOL-4-YLACETAMIDES AS POST EMERGENT SELECTIVE HERBICIDES

This is a division of U.S. Ser. No. 937,290, filed Aug. 28, 1978.

DESCRIPTION OF THE INVENTION

Ali et al. in *The Journal of Chemical and Engineering Data*, vol. 17, p. 106 (1972) reported that 4-bromoacetoacetanilide and thiourea in refluxing ethanol yielded to the corresponding 2-aminothiazole hydrobromide. Treatment with ammonium hydroxide yielded 50% 2-aminothiazol-4-ylacetic acid anilide, m.p. 152°–54°.

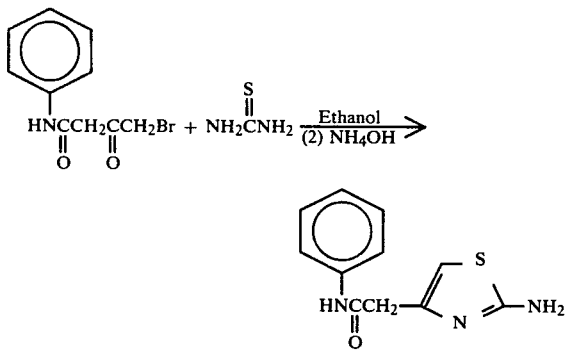

This general class of aminothiazolylacetanilides, including compounds with various substituents on the phenyl ring are non-phytotoxic and in fact appear to have no effect on plant life at all. I have discovered, however, that when an acyl or carbamoyl substituent is attached to the free amino group, the resulting compounds are useful as post-emergent selective herbicides. I have further discovered that a class of compounds which are useful as both pre- and post-emergent herbicides have the general formula

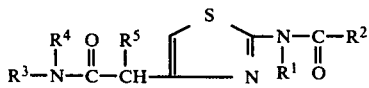

in which $R^1$ in hydrogen or methyl, $R^2$ is ethyl, isopropyl, cyclopropyl, tert.butyl, methylamino, dimethylamino, ethylamino or methoxymethylamino, $R^3$ is phenyl, 4-chlorophenyl, 3,4-dichlorophenyl, 4-methylphenyl or 4-methoxyphenyl, $R^4$ is hydrogen or $C_1$ to $C_3$ lower alkyl and $R^5$ is hydrogen or methyl, with the further stipulation that either, but not both $R^4$ and $R^5$ may be hydrogen. The herbicides of this class are applied both pre- and post-emergently to the locus of unwanted vegetation so as to obtain selective control of said vegetation in fields of agricultural crops. The new herbicides of this invention are particularly useful in controlling lambs-quarters, pigweed and wild mustard, both pre- and post-emergently.

Synthesis of the Herbicides

The starting materials employed in synthesis of the compounds of this invention are various acetoacetanilides derived from substituted anilines which have replaceable hydrogen by reaction with ethyl acetoacetate or diketene or an approximately 50 percent acetone solution of diketene. Bromination of the acetoacetamides in acetic acid reaction medium produces almost exclusively the corresponding 4-bromoacetoacetamides. The latter compounds are stable intermediates which react with thiourea or N-substituted thiourea in the presence of an acid scavenger in ethanol reaction medium to give the corresponding aminothiazolylacetamides in good yields. Reaction with various available acylating agents or alkyl isocyanates then yields the herbicides of this invention. Illustrative synthesis procedures are exemplified below.

Preparation of 4-(4-chlorophenylcarbamoylethylidene)-2-isobutyramido thiazole A 300 ml reaction flask fitted with a magnetic stirrer, heating mantle, thermometer and water-cooled condenser was charged with 5.0 g (0.016 mole) of 4-bromo-4'-chloro-2-methylacetoacetanilide [M.P. 103°–105°; prepared as described by Hodgkinson and Staskun in *The Journal of Organic Chemistry*, vol. 34, p. 1710 (1969)], 100 ml of ethanol, 2.5 g (0.017 mole) of N-isobutyrylthiourea [M.P. 112°–114°; prepared as described by Moore and Crossley in *The Journal of the American Chemical Society*, vol. 62, p. 3273 (1940)] and 1.6 g (0.02 mole) of pyridine. The solution was stirred and refluxed for three hours. The solvent was removed under reduced pressure and the residual solid was stirred with watertoluene. There was obtained 3.9 g (69%) of white solid, M.P. 202°–204°. N.M.R. (dimethyl-$d_6$ sulfoxide) ∂1.1–1.3 (2×$CH_3$), 1.4–1.6 ($CH_3$, doublet), 3.5–4.0 (2×CH), 6.8 (hetero-aromatic), 7.2–7.7 (aromatic).

Preparation of 4-(4-chlorophenylcarbamoylethylidene)-2-(3-methylureido)thiazole A reaction flask was charged with 3.9 g (0.011 mole) of 2-amino-4-(4-chlorophenylcarbamoylethylidene) thiazole hydrobromide (M.P. 112°–16°; prepared from 4-bromo-4'-chloro-2-methylacetoacetanilide and thiourea in ethanol), 30 ml of pyridine and 1.1 g (0.018 mole) of methyl isocyanate. The solution was allowed to stir overnight at ambient temperature. On the following morning, the pyridine solution was poured into water. The water was decanted from the residual oil. With stirring, the addition of fresh water caused the residue to solidify. The solid was dissolved in hot ethanol. The crystalline material in the cooled mixture was collected on a vacuum filter. There was obtained 1.4 g (38%) of white solid, M.P. 203°–205°. N.M.R. (dimethyl-$d_6$ sulfoxide, $CDCl_3$) ∂1.3–1.6 ($CH_3$, doublet), 2.5–2.8 ($NCH_3$, doublet), 3.5–3.8 (CH), 6.5 (hetero-aromatic), 7.1–7.7 (aromatic), 9.9 and 10.4 [NHC(O)NH].

Preparation of 4'-chloro-N-methylacetoacetanilide

An appropriately fitted reaction flask was charged with 26.5 g (0.187 mole) of 4-chloro-N-methylaniline [prepared as described by Kadin in *The Journal of Organic Chemistry*, vol. 38, p. 1348 (1973)] and 90 ml of 1,2-dichloroethane. Dropwise addition of 16.7 g (0.2 mole) of diketene produced an exothermic response. The reaction solution was refluxed for four hours. Additional 1,2-dichloroethane was added and the organic phase was extracted with: (a) dilute hydrochloric acid, (b) water and (c) saturated aqueous sodium chloride. After drying the 1,2-dichloroethane solution over sodium sulfate, the solvent was evaporated under an efficient source of vacuum. The residual oil (38.9 g, 92%) was used in the following reaction without further purification. N.M.R. (CDCl₃) ∂1.8 (CH₃, enol), 2.2 (CH₃, keto), 3.2 (NCH₃), 3.7 (CH₂), 4.8 (CH), 7.2–7.4 (aromatic).

Preparation of 4-bromo-4'-chloro-N-methylacetoacetanilide

A 500 ml reaction flask fitted with a condenser, drying tube, magnetic stirrer, thermometer and dropping funnel was charged with 38.9 g (0.172 mole) of 4'-chloro-N-methylacetoacetanilide and 350 ml of glacial acetic acid. The dropping funnel contained 27.5 g (0.172 mole) of bromine and a crystal of iodine dissolved in 85 ml of acetic acid. The bromination solution was added dropwise over 45 minutes to the stirred reaction solution while maintaining a pot temperature of about 25°. The solution was allowed to stir at ambient temperature for 48 hours. The acetic acid solution was poured into 800 ml of cold water. The aqueous mixture was twice extracted with 400 ml of ether. The combined ether extracts were washed with water and dried over sodium sulfate. The solvent was removed on the rotary evaporator to give a residual liquid (40.4 g, 77%) which was used in subsequent reactions without further purification. N.M.R. (CDCl₃) ∂3.2 (NCH₃), 3.7 (O=C CH₂C=O), 4.0 (O=CCH₂Br), 5.0 (CH, enol), 7.2–7.4 (aromatic).

Preparation of 2-amino-4-[N-4-chlorophenyl-N-methyl(carbamoylmethyl)] thiazole A 500 ml reaction flask equipped with a condenser, magnetic stirrer, thermometer and heating mantle was charged with 20.2 g (0.066 mole) of 4-bromo-4'-chloro-N-methylacetoacetanilide, 200 ml of ethanol and 5.4 g (0.071 mole) of thiourea. The reaction solution was refluxed for three hours. After cooling, about one-half of the solvent was removed on the rotary evaporator and the solution was poured into 300 ml of water. After adding sufficient ammonium hydroxide to pH 8, additional water was added. The precipitated crystalline product was dried in a vacuum oven. There was obtained 12.4 g (66.7%) of white material, M.P. 148°–50°. N.M.R. (dimethyl-d₆ sulfoxide, CDCl₃) ∂3.2 (NCH₃), 3.3 (CH₂), 6.0 (heteroaromatic), 7.3–7.5 (aromatic).

Preparation of 4-[N-4-chlorophenyl-N-methyl)Carbamoylmethyl)]-2-propionamidothiazole A 300 ml reaction flask was charged with 6.0 g (0.021 mole) of 2-amino-4-[N-4-chlorophenyl-N-methyl(carbamoylmethyl)] thiazole, 100 ml of 1,2-dimethoxyethane and 2.6 g (0.03 mole) of pyridine. The propionyl chloride (2.8 g, 0.03 mole) which was dissolved in 15 ml of 1,2-dimethoxyethane was added portionwise and the reaction solution was heated at 65° for two hours. The solvent was evaporated and the residue was dissolved in ethyl acetate. The organic phase was extracted with water and dried over sodium sulfate. After evaporating most of the ethyl acetate, hexane was added. There was obtained 3.7 g (51%) of product, M.P. 153°–5°. N.M.R. (CDCl₃) ∂1.2–1.4 (CH₃), 2.3–2.5 (CH₂), 3.3 (NCH₃), 3.5 (O=CCH₂), 6.5 (hetero-aromatic) 7.2–7.4 (aromatic).

Preparation of N-isopropyl-4'-chloroacetoacetanilide

A 500 ml reaction flask fitted with a condenser, drying tube, magnetic stirrer and therometer was charged with 89.5 g (0.528 mole) of 4-chloro-N-isopropylaniline, 200 ml of glacial acetic acid and 18.5 g (0.58 mole) of mercuric acetate. To the stirred solution there was added dropwise 48.8 g (0.58 mole) of diketene while the reaction temperature was maintained at 30°–5°. The reaction solution was allowed to stir overnight at ambient temperature. The solution was mixed with two liters of water and twice extracted with ether. The organic phase was washed with water and dried over sodium sulfate. After removing the solvent, the liquid residue weighed 134 g (100%). N.M.R. (CDCl₃) ∂1.0 and 1.2 (isopropyl, doublet), 1.8 (CH₃, enol), 2.1 (CH₃, keto), 3.2 (CH₂), 4.7–5.2 (CH, isopropyl), 7.1–7.5 (aromatic).

Preparation of N-isopropyl-4'-chloro-2-methylacetoacetanilide

A one liter reaction flask equipped with a power stirrer, condenser, drying tube, thermometer and nitrogen inlet tube was charged with 48.5 g (0.19 mole) of N-isopropyl-4'-chloroacetoacetanilide and 145 ml of dry dimethylformamide. With efficient stirring in a nitrogen atmosphere, portionwise addition of 7.2 g of 57% sodium hydride in mineral oil (0.17 mole) was completed in one hour (excessive foaming). Methyl iodide (24.1 g, 0.17 mole) was added dropwise and the reaction mixture was stirred for two hours at ambient temperature. The mixture was poured into one liter of cold water and stirred. The organic material was extracted into toluene and the latter was water washed. Most of the toluene was removed on the rotary evaporator. Hexane was added which caused the mass to crystallize. There was obtained 36.4 g (80%) of white material, M.P. 77°–79°. N.M.R. (CDCl₃) ∂0.9–1.4 (CH₃, 9 protons), 2.0 (O=C-CH₃), 2.9–3.2 (CH), 4.7–5.2 (CH, isopropyl), 6.9–7.5. (aromatic).

Preparation of N-isopropyl-4'-chloro-4-bromo-2-methylacetoacetanilide

To a reactio flask which contained 71.6 g (0.267 mole) of N-isopropyl-4'-chloro-2-methylacetoacetanilide dissolved in 360 ml of glacial acetic acid, there was added dropwise a solution of 42.7 g (0.267 mole) of bromine in 30 ml of acetic acid. The solution was stirred overnight at ambient temperature. On the following morning, the reaction solution was added to two liters of cold water and the organic material was extracted into toluene. The latter was washed with water and dried over sodium sulfate. After removal of the solvent, there was obtained 86.6 g (97%) of residual oil. N.M.R. (CDCl₃)∂0.9–1.4 (CH₃, 9 protons), 3.3–3.6 (CH), 3.9–4.0 (CH₂Br), 4.8–5.2 (CH, isopropyl), 7.1–7.6 (aromatic).

Preparation of 2-amino-4-[N-4-chlorophenyl-N-isopropyl (carbamoylethylidene)] thiazole A solution containing 43.3 g (0.13 mole) of N-isopropyl-4'-chloro-4-bromo-2-methylacetoacetanilide, 10.2 g (0.14 mole) of thiourea and 300 ml of ethanol was refluxed for two hours. A portion of the ethanol was evaporated and water was added. The reaction solution was made basic with ammonium hydroxide. After drying, the white solid weighed 33 g (78%), M.P. 145°–47°. N.M.R. (dimethyl-d₆ sulfoxide, CDCl₃) ∂0.9–1.3 (CH₃, 9 protons), 3.1–3.4 (CH), 4.6–5.1 (CH, isopropyl), 5.9 (hetero-aromatic), 6.5 (NH₂), 7.0–7.5 (aromatic).

Preparation of 4-[N-4-chlorophenyl-N-isopropyl(carbamoylethylidene.)]-2-(3-methylureido) thiazole A solution of 5.5 g (0.017 mole) of 2-amino-4-[N-4-chlorophenyl-N-isopropyl (carbamoylethylidene)] thiazole, 1.3 g (0.022 mole) of methyl isocyanate in toluene was heated at 45° for 12 hours. The solvent was evaporated and the gummy residue was stirred with heptane. After 10 hours, crystallization appeared to be complete. There was obtained 2.5 g (39%) of white solid, M.P. 111°–14°. N.M.R. (CDCl$_3$) ∂0.8–14. (CH$_3$, 9 protons), 2.8–2.9 (NCH$_3$), 3.4–3.7 (CH), 4.8–5.1 (CH, isopropyl), 6.3 (hetero-aromatic), 6.8–7.4 (aromatic), 9.8 (O=CNH).

Compounds which have been made by means of the procedures illustrated above are listed in the following table.

scribed below to illustrate selective control of unwanted vegetation.

Procedure

An aqueous dispersion of each active compound was prepared by combining 0.4 gram of the compound with about 4 ml of a solvent-emulsifier mixture (3 parts of a commercial polyoxyethylated vegetable oil emulsifier, one part xylene, one part kerosene) and then adding water, with stirring, to a final volume of 40 ml.

The species of plants on which each compound was tested were planted in disposable plastic pots in a greenhouse. Ten to eighteen days after emergence of the plants, three pots of each species were sprayed at each application rate with an aqueous dispersion of the active compound prepared as described above, at rates of both 1 lb. and 3 lb. of active compound per acre and at a spray volume of 40 gal. per acre. Approximately one Compounds of the Formula

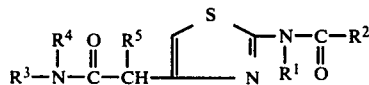

| Compound No. | R$^1$ | R$^2$ | R$^3$ | R$^4$ | R$^5$ | Physical Property |
|---|---|---|---|---|---|---|
| 1 | —CH$_3$ | —NHCH$_3$ | phenyl | —CH$_3$ | H | thick oil |
| 2 | —H | —NHCH$_3$ | 4-chlorophenyl | —H | —CH$_3$ | m.p. 203–205° |
| 3 | —H | —N(CH$_3$)$_2$ | 4-chlorophenyl | —H | —CH$_3$ | m.p. 65–70° |
| 4 | —H | —NHC$_2$H$_5$ | 4-chlorophenyl | —H | —CH$_3$ | m.p. 202–204° |
| 5 | —CH$_3$ | —NHCH$_3$ | 4-chlorophenyl | —H | —CH$_3$ | m.p. 172–174° |
| 6 | —H | —NHCH$_3$ | 4-chlorophenyl | —CH(CH$_3$)$_3$ | —H | m.p. 65–70° (dec.) |
| 7 | —H | —NHCH$_3$ | 4-chlorophenyl | —CH(CH$_3$)$_2$ | —CH$_3$ | m.p. 111–114° |
| 8 | —H | —N(CH$_3$)$_2$ | 4-chlorophenyl | —CH(CH$_3$)$_2$ | —CH$_3$ | m.p. 72–75° |
| 9 | —CH$_3$ | NHCH$_3$ | 4-chlorophenyl | —CH(CH$_3$)$_2$ | —CH$_3$ | m.p. 74–77° |
| 10 | —H | —CH(CH$_3$)$_3$ | 4-chlorophenyl | —H | —CH$_3$ | m.p. 202–204° |
| 11 | —H | —C(CH$_3$)$_3$ | 4-chlorophenyl | —H | —CH$_3$ | m.p. 193–195° |
| 12 | —H | cyclopropyl | 4-chlorophenyl | —H | —CH$_3$ | m.p. 219–222° |
| 13 | —H | —C$_2$H$_5$ | 4-chlorophenyl | —CH$_3$ | —H | m.p. 153–155° |
| 14 | —H | —C$_2$H$_5$ | phenyl | —CH$_3$ | —H | m.p. 141–143° |
| 15 | —H | —C$_2$H$_5$ | 4-methylphenyl | —CH$_3$ | —H | m.p. 149–150° |
| 16 | —H | —NHCH$_3$ | 4-chlorophenyl | —CH$_3$ | —H | m.p. 65–75° |
| 17 | —CH$_3$ | CH$_3$<br>\|<br>—N—OCH$_3$ | 4-chlorophenyl | —CH$_3$ | —H | thick oil |
| 18 | —CH$_3$ | —N(CH$_3$)$_2$ | 4-chlorophenyl | —CH$_3$ | —H | thick oil |
| 19 | —H | —NHCH$_3$ | 3,4-dichlorophenyl | —CH(CH$_3$)$_2$ | —H | m.p. 94–97° |
| 20 | —H | —NHCH$_3$ | 3,4-dichlorophenyl | —CH(CH$_3$)$_2$ | —CH$_3$ | m.p. 80–85° |
| 21 | —H | —NHCH$_3$ | 4-methylphenyl | —CH$_3$ | —H | m.p. 74–78° |
| 22 | —H | —NHCH$_3$ | 4-methoxyphenyl | —CH$_3$ | —H | m.p. 61–65° |

Selectively Combating Unwanted Vegetation

The novel herbicides are particularly effective when used both pre-and post-emergently against broadleaved weeds in grain fields. Greenhouse tests are deweek after the spray application the plants were observed and phytotoxicity was rated according to the following schedule.
0—no control or injury
1—1 to 25 percent control or injury 2—26 to 75 percent control or injury
3—76 to 99 percent control or injury
4—complete control or kill The same rating schedule was employed to judge pre-emergent results obtained according to the procedure below.

A solution of each active compound was prepared by dissolving 290 mg of the compound to be tested in 200 ml of acetone. Disposable paper trays about 2½ inches deep were filled with soil and sprayed with the acetone solution at rates of 3 lb. and 1 lb. of active chemical per acre of sprayed area, were seeded with the test species of plant seeds and were then covered with about ¼ inch of soil. Twenty-one days after seeding and treatment the plantings were examined and herbicidal effect was rated according to the above schedule.

RESULTS OF HERBICIDAL USE

| PLANT SPECIES | Appl'n. Rate (lb./A.) | 1 Pre | 1 Post | 2 Pre | 2 Post | 3 Pre | 3 Post | 4 Pre | 4 Post | 5 Pre | 5 Post | 6 Pre | 6 Post | 7 Pre | 7 Post |
|---|---|---|---|---|---|---|---|---|---|---|---|---|---|---|---|
| Xanthium pensylvanicum | 3 | | 4 | 1 | 0 | | 4 | | 0 | 0 | 4 | 0 | 4 | | 3 |
| Cocklebur | 1 | | 2 | | | | 4 | | | | 4 | | 1 | | 1 |
| Chenopodium album | 3 | | 4 | 3 | 4 | | 4 | — | 4 | 4 | 4 | 4 | 4 | | 4 |
| Lambsquarters | 1 | | 4 | | | | 4 | | | | 4 | | 4 | | 4 |
| Ipomoea purpurea | 3 | | 4 | 0 | 0 | | 4 | | 0 | 0 | 4 | 0 | 3 | | 2 |
| Morning Glory | 1 | | 2 | | | | 2 | | | | 2 | | 0 | | 0 |
| Amaranthus retroflexus | 3 | | 4 | 4 | 3 | | 4 | | 2 | 4 | 4 | 4 | 4 | | 3 |
| Pigweed | 1 | | 4 | | | | 4 | | | | 4 | | 3 | | 1 |
| Polygonum convolvulus | 3 | | 4 | 4 | 2 | | 4 | | 4 | 4 | 4 | 3 | 4 | | 4 |
| Wild Buckwheat | 1 | | 4 | | | | 4 | | | | 3 | | 4 | | 4 |
| Brassica kaber | 3 | | 4 | 2 | 4 | | 4 | | 2 | 4 | 4 | 4 | 4 | | 3 |
| Wild Mustard | 1 | | 2 | | | | 4 | | | | 4 | | 4 | | 4 |
| Medicago sativa | 3 | | 4 | 4 | 1 | | 4 | | 1 | 3 | 4 | 2 | 4 | | 4 |
| Alfalfa | 1 | | 3 | | | | 4 | | | | 4 | | 2 | | 4 |
| Gossypium herbaceum | 3 | | 2 | 2 | 0 | | 4 | | 1 | 0 | 4 | 0 | 3 | | 1 |
| Cotton | 1 | | 1 | | | | 4 | | | | 3 | | 2 | | 1 |
| Arachia hypogae | 3 | | 0 | 0 | 0 | | 1 | | 0 | 0 | 1 | 0 | 2 | | 1 |
| Peanut | 1 | | 0 | | | | 0 | | | | 1 | | 1 | | 1 |
| Soja mar | 3 | | 4 | 1 | 0 | | 4 | | 1 | 0 | 4 | 0 | 4 | | 3 |
| Soybean | 1 | | 3 | | | | 2 | | | | 4 | | 3 | | 1 |
| Zea mays | 3 | | 1 | 0 | 0 | | 0 | | 0 | 0 | 0 | 0 | 0 | | 0 |
| Corn | 1 | | 0 | | | | 0 | | | | 0 | | 0 | | 0 |
| Sorghum vulgare | 3 | | 2 | 0 | 0 | | 1 | | 0 | 0 | 1 | 0 | 0 | | 0 |
| Grain Sorghum | 1 | | 0 | | | | 0 | | | | 0 | | 0 | | 0 |
| Oryza sativa | 3 | | 2 | 0 | 0 | | 1 | | 0 | 0 | 2 | — | 1 | | 1 |
| Rice | 1 | | 0 | | | | 0 | | | | 1 | | 0 | | 0 |
| Triticam aestivum | 3 | | 4 | 1 | 0 | | 2 | | 0 | 1 | 3 | 0 | 2 | | 3 |
| Wheat | 1 | | 1 | | | | 1 | | | | 1 | | 1 | | 1 |

| PLANT SPECIES | Appl'n. Rate (lb./A.) | 8 Pre | 8 Post | 9 Pre | 9 Post | 10 Pre | 10 Post | 11 Pre | 11 Post | 12 Pre | 12 Post | 13 Pre | 13 Post | 14 Pre | 14 Post | 15 Pre | 15 Post |
|---|---|---|---|---|---|---|---|---|---|---|---|---|---|---|---|---|---|
| Xanthium pensylvanicum | 3 | | 4 | 4 | 4 | 1 | | | 4 | | 4 | 0 | 4 | 0 | 3 | | 4 |
| Cocklebur | 1 | | 3 | | 2 | | 0 | | 1 | | 3 | | 4 | | 2 | | 2 |
| Cheropodium album | 3 | | 3 | 4 | 4 | 4 | | | 4 | | 4 | 4 | 4 | 4 | 4 | | 4 |
| Lambsquarters | 1 | | 2 | | 4 | | 4 | | 4 | | 4 | | 4 | | 4 | | 4 |
| Isomaea purpurea | 3 | | 3 | 4 | 4 | 1 | | | 2 | | 4 | 1 | 4 | 3 | 4 | | 4 |
| Morning Glory | 1 | | 1 | | 1 | | 1 | | 1 | | 3 | | 4 | | 3 | | 2 |
| Amaranthus retroflexus | 3 | | 1 | 3 | 4 | 3 | | | 4 | | 4 | 4 | 4 | 4 | 4 | | 4 |
| Pigweed | 1 | | 1 | | 4 | | 1 | | 3 | | 2 | | 4 | | 3 | | 3 |
| Polyganum convolvulus | 3 | | 3 | 4 | 4 | 4 | | | 4 | | 4 | 2 | 4 | 0 | 4 | | 4 |
| Wild Buckwheat | 1 | | 3 | | 4 | | 2 | | 3 | | 4 | | 4 | | 4 | | 4 |
| Brassica kaber | 3 | | 3 | 4 | 4 | 4 | | | 4 | | 4 | 4 | 4 | 4 | 4 | | 4 |
| Wild Mustard | 1 | | 3 | | 4 | | 1 | | 4 | | 4 | | 4 | | 4 | | 1 |
| Medicago sativa | 3 | | 3 | 4 | 0 | 1 | | | 4 | | 4 | 4 | 4 | 4 | 3 | | 4 |
| Alfalfa | 1 | | 1 | | 3 | | 1 | | 1 | | 3 | | 4 | | 1 | | 3 |
| Gossypium herbaceum | 3 | | 2 | 3 | 0 | 2 | | | 4 | | 2 | 1 | 4 | 0 | 4 | | 4 |

-continued

RESULTS OF HERBICIDAL USE

| Plant | Rate | | | | | | | | | |
|---|---|---|---|---|---|---|---|---|---|---|
| Cotton | 1 | 2 | 2 | 1 | 1 | 2 | 4 | 4 | 3 | |
| *Arachia hypogae* | 3 | 1 | — | 0 | 0 | 0 | 0 | 0 | 2 | 0 | 1 | 1 |
| Penaut | 1 | 0 | 1 | | 0 | 0 | 0 | | 1 | | 0 | 0 |
| *Soja mar* | 3 | 3 | 4 | 0 | 2 | 4 | 3 | 0 | 4 | 1 | 3 | 4 |
| Soybean | 1 | 3 | 2 | | 1 | 1 | 3 | | 3 | | 2 | 3 |
| *Zea mays* | 3 | 0 | 1 | 0 | 0 | 0 | 0 | 0 | 2 | 0 | 0 | 1 |
| Corn | 1 | 0 | 0 | | 0 | 0 | 0 | | 1 | | 0 | 1 |
| *Sorghum vulgare* | 3 | 0 | 1 | 0 | 0 | 0 | 0 | 0 | 3 | 0 | 1 | 1 |
| Grain Sorghum | 1 | 0 | 1 | | 0 | 0 | 0 | | 2 | | 0 | 0 |
| *Oryza satvia* | 3 | 1 | 2 | 4 | 0 | 0 | 1 | 0 | 3 | 0 | 2 | 4 |
| Rice | 1 | 0 | 0 | | 0 | 0 | 0 | | 1 | | 0 | 0 |
| *Triticum aestivum* | 3 | 2 | 3 | 4 | 0 | 1 | 1 | 0 | 4 | 0 | 3 | 2 |
| Wheat | 1 | 0 | 2 | | 0 | 0 | 0 | | 3 | | 1 | 0 |

| | Appl'n. Rate (lb./A.) | Compound No. | | | | | | | | | | | | |
|---|---|---|---|---|---|---|---|---|---|---|---|---|---|---|
| | | 16 | | 17 | | 18 | | 19 | | 20 | | 21 | | 22 | |
| PLANT SPECIES | | Pre | Post | Pre | Post | Pre | Post | Pre | Post | Pre | Post | Pre | Post | Pre | Post |
| *Xanthium pensylvanicum* | 3 | | 4 | — | — | | — | 4 | 0 | 4 | | 4 | | 4 | |
| Cocklebur | 1 | | 4 | | | | — | 3 | | 2 | | 2 | | 4 | |
| *Chenopodium album* | 3 | | 4 | 4 | 4 | 4 | | 4 | 4 | 4 | | 4 | | 4 | |
| Lambsquarters | 1 | | 4 | | | 4 | | 4 | | 4 | | 4 | | 4 | |
| *Ipomoea purpurea* | 3 | | 4 | 3 | 0 | — | | 2 | 0 | 3 | | 4 | | 4 | |
| Morning Glory | 1 | | 4 | | | 4 | | 2 | | 1 | | 4 | | 4 | |
| *Amaranthus retroflexus* | 3 | | 4 | 3 | 4 | 4 | | 3 | 2 | 2 | | 4 | | 4 | |
| Pigweed | 1 | | 4 | | | 4 | | 3 | | 3 | | 4 | | 4 | |
| *Polygonum convolvulus* | 3 | | 4 | 3 | 4 | 4 | | 4 | 4 | 4 | | 4 | | 4 | |
| Wild Buckwheat | 1 | | 4 | | | 4 | | 4 | | 4 | | 3 | | 4 | |
| *Brassica kaber* | 3 | | 4 | 2 | 4 | 4 | | 4 | 4 | 4 | | 4 | | 4 | |
| Wild Mustard | 1 | | 4 | | | 4 | | 4 | | 4 | | 4 | | 4 | |
| *Medicago sativa* | 3 | | 4 | 1 | 4 | 4 | | 3 | 2 | 4 | | 4 | | 4 | |
| Alfalfa | 1 | | 4 | | | 4 | | 3 | | 4 | | 3 | | 3 | |
| *Gossypium herbaceum* | 3 | | 2 | 2 | 0 | 4 | | 3 | 0 | 4 | | 3 | | 4 | |
| Cotton | 1 | | 3 | | | 4 | | 2 | | 1 | | 4 | | 4 | |
| *Arachia hypogaea* | 3 | | 1 | 0 | 0 | 1 | | 1 | 0 | 1 | | 1 | | 1 | |
| Peanut | 1 | | 1 | | | 1 | | 0 | | 0 | | 0 | | 0 | |
| *Soja mar* | 3 | | 4 | 3 | 1 | 4 | | 4 | 0 | 4 | | 4 | | 4 | |
| Soybean | 1 | | 4 | | | 3 | | 3 | | 2 | | 3 | | 3 | |
| *Zea mays* | 3 | | 1 | 0 | 0 | 2 | | 0 | 0 | 0 | | 0 | | 1 | |
| Corn | 1 | | 1 | | | 1 | | 0 | | 0 | | 0 | | 0 | |
| *Sorghum vulgare* | 3 | | 1 | 0 | 0 | 3 | | 0 | 0 | 0 | | 0 | | 1 | |
| Grain Sorghum | 1 | | 1 | | | 2 | | 0 | | 0 | | 0 | | 0 | |
| *Oryza sativa* | 3 | | 2 | 0 | 1 | 2 | | 0 | — | 0 | | 0 | | 1 | |
| Rice | 1 | | 1 | | | 1 | | 0 | | 0 | | 0 | | 0 | |
| *Triticum aestivum* | 3 | | 3 | 1 | 0 | 2 | | 0 | 0 | 1 | | 1 | | 2 | |
| Wheat | 1 | | 3 | | | 2 | | 0 | | 1 | | 0 | | 1 | |

The method of selectively combating unwanted vegetation according to this invention comprises the step of applying to the locus of unwanted vegetation an effective amount of a compound having the general structural formula

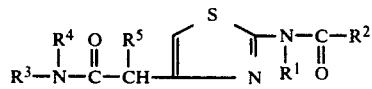

in which $R^1$ is hydrogen or methyl, $R^2$ is ethyl, isopropyl, cyclopropyl, tert.butyl, methylamino, dimethylamino, ethylamino or methoxymethylamino, $R^3$ is phenyl, 4-chlorophenyl, 3,4-dichlorophenyl, 4-methylphenyl or 4-methoxyphenyl, $R^4$ is hydrogen or $C_1$ to $C_3$ lower alkyl and $R^5$ is hydrogen or methyl, with the further stipulation that either, but not both $R^4$ and $R^5$ may be hydrogen. The test results disclosed above serve to illustrate the selectivity and efficacy of the novel herbicides, so that a choice can be made of the compound and rate of application to suit a specific weed problem in a particular crop. The method is particularly desirable for combating broad-leaved weeds in peanuts, corn, grain sorghum and wheat crops. It will be understood that a final selection of application rates is best made after outdoor tests under the conditions of application, soil and climate which will actually be encountered in the field. In general, outdoor application is done less efficiently than under the controlled conditions of a greenhouse laboratory and so somewhat higher rates of application are required.

It will be understood that the term "selectively combating" means killing or otherwise injuring the unwanted vegetation to a degree which is beneficial to the crop.

I claim:

1. The method of selectively combating unwanted vegetation which comprises applying to the locus of the unwanted vegetation an effective amount of a selectively phytotoxic compound having the general structural formula

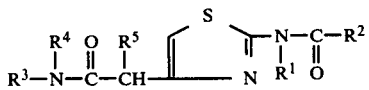

in which $R^1$ is hydrogen or methyl, $R^2$ is ethyl, isopropyl, cyclopropyl, tert.butyl, methylamino, dimethylamino, ethylamino or methoxymethylamino, $R^3$ is phenyl, 4-chlorophenyl, 3,4-dichlorophenyl, 4-methylphenyl or 4-methoxyphenyl, $R^4$ is hydrogen or $C_1$ to $C_3$ lower alkyl and $R^5$ is hydrogen or methyl, with the further stipulation that either, but not both $R^4$ and $R^5$ may be hydrogen.

2. The method according to claim 1 in which $R^1$ is methyl, $R^2$ is methylamino, $R^3$ is 4-chlorophenyl, $R^4$ is hydrogen and $R^5$ is methyl.

3. The method according to claim 1 in which $R^1$ is methyl, $R^2$ is dimethylamino, $R^3$ is 4-chlorophenyl, $R^4$ is methyl and $R^5$ is hydrogen.

4. The method according to claim 1 in which $R^1$ is hydrogen, $R^2$ is ethyl, $R^3$ is 4-chlorophenyl, $R^4$ is methyl and $R^5$ is hydrogen.

5. The method according to claim 1 in which $R^1$ is hydrogen, $R^2$ is methylamino, $R^3$ is 4-chlorophenyl, $R^4$ is methyl and $R^5$ is hydrogen.

6. The method according to claim 1 in which $R^1$ is hydrogen, $R^2$ is methylamino, $R^3$ is 4-methylphenyl, $R^4$ is methyl and $R^5$ is hydrogen.

7. The method according to claim 1 in which $R^1$ is hydrogen, $R^2$ is methylamino, $R^3$ is 4-methoxyphenyl, $R^4$ is methyl and $R^5$ is hydrogen.

* * * * *